United States Patent [19]

Fedorov

[11] Patent Number: 4,953,969

[45] Date of Patent: Sep. 4, 1990

[54] DEVICE FOR CORRECTING OCULAR REFRACTION ANOMALIES

[76] Inventor: Svyatoslav N. Fedorov, pereulok Dostoevskogo, I/2I,kv.32., Moscow, U.S.S.R.

[21] Appl. No.: 378,030

[22] Filed: Jul. 11, 1989

[30] Foreign Application Priority Data

Jul. 11, 1988 [SU] U.S.S.R. ............................ 4457772

[51] Int. Cl.$^5$ .............................................. A61B 3/10
[52] U.S. Cl. .................................... 351/221; 351/246; 606/5
[58] Field of Search ....................... 351/205, 221, 246; 606/4, 5, 6; 128/395

[56] References Cited

U.S. PATENT DOCUMENTS 4,669,837  6/1987  Schrimer ............................. 351/221

Primary Examiner—Rodney B. Bovernick
Attorney, Agent, or Firm—Burgess, Ryan & Wayne

[57] ABSTRACT

The device comprises optically interconnected components such as an ultraviolet pulsed laser operating at a wavelength of 223 nm, a uniform light beam former, a slotted mask with its rotation drive, and a means for forming the image of the slotted mask on a surface of the cornea of the eye. The slotted mask having at least two slots shaped as identical lobes provides in rotation for uniform axysymmetric distribution of ultraviolet radiation over the exposed surface of the cornea. Arranged at the optical outlet of the former are a unit used to monitor energy density of ultraviolet radiation and a microscope.

29 Claims, 4 Drawing Sheets

DEVICE FOR CORRECTING OCULAR REFRACTION ANOMALIES

FIELD OF THE INVENTION

The present invention relates to means for treatment and protection of eyes, more particularly, to devices for correcting ocular refraction anomalies.

The invention can find applications in ophthalmology, for example, in correction of myopia and hypermetropia.

BACKGROUND ART

Known in the art is a method of correction ocular refraction anomalies which comprises supplying of pulsed ultraviolet radiation with a wavelength of 193 nm on the cornea surface and evaporation of the cornea in layers until obtaining required correction of refraction anomalies. (Lasers in Ophthalmology, vol. I, N1, 1986, Amsterdam, J. Marshall, S. Trakel, S. Rothery, R. R. Krueger "Photoablative" reprofiling of the cornea using an eximer laser. Photorefractive keratectomy, p. 21).

The speed of evaporation of the cornea at said wavelength of radiation is negligible which calls for a greater number of pulses fed. And since the human eye is a live object, any delay in operation can lead to the loss of accuracy.

Known in the art is a method for treating myopia, which comprises evaporation of the cornea in layers, using pulsed ultraviolet radiation with a wavelength of 193 nm through a rotating slotted mask. With due regard for losses in the optical system from a laser energy of 167 mJ it is mere 4.5 mJ that gets to the surface of the cornea with a density of 200 mJ/cm$^2$ which exceeds the threshold value for the cornea ablation by a factor of two. What is optimal, however, is a higher range of energy densities so that without increasing the degree of thermal corneal injury to attain maximum rate of the tissue ablation. For this purpose, there is needed a laser with a radiation energy of 334–835 mJ at a wavelength of 193 nm, which in addition to technical difficulties of developing the laser per se has a great energy consumed and large overall dimensions, which may be reflected on the conditions of arranging the apparatus in the operation room (K. Hanna, J. C. Chastang, Y. Pouliquen, G. Renard and L. Asfar, Excimer Laser Refractive Keratoplasty, Paris, 1986, p. 1, 3).

It is worthy of note that the human eye is a movable object and can be constructed and displaced in the period of pulsed influence which impairs the accuracy of correction and is likely to cause astigmatism.

A known device for performing ophthalmologic operations by a photoevaporation method comprises a solidstate laser having an operating wavelength of 150 to 220 nm and such optically interconnected components as a controlled shutter, an optical section, an electric or acoustic modulator and a radiation wavelength converter (cf. PCT WO 87/00748).

Optical facilities of such a device are difficult to manufacture and control. The foregoing device calls for additional wavelength conversion and ensures point treatment of the corneal surface, which generally involves a complicated time-consuming procedure in obtaining a desired profile since the number of transmitted pulses is fairly great.

There is also known a device comprising an ultraviolet pulsed laser having an operating wavelength of 193 nm and such optically interconnected components as a uniform light beam former, a slotted mask having one slot shaped as a lobe, and a means for forming the mask image on the surface of the cornea. The slotted mask is provided with a drive enabling its rotation, a feature providing for axisymmetric distribution of radiation over the exposed surface of the cornea.

The disclosed device also comprises a microscope used to observe the emission of radiation to the surface of the cornea and the correction process, said microscope being optically connected with the image former, and a unit designed to monitor energy density of radiation incident on the surface of the cornea and arranged at the optical outlet of the image former (cf. K. Hanna, Jc. Chastang, J. Pouliquen, G. Renard, Z. Asfar: "Exciter laser refractive keratoplasty", 1986, Paris, p. 1).

The provision of one slot in the slotted mask does not permit increasing the correction speed since the pulse recurrence rate is positively limited by a cumulative thermal effect, a disadvantage increasing traumatism of biologic tissue.

SUMMARY OF THE INVENTION

It is an object of the present invention to create a device for correcting ocular refraction anomalies, which would make it possible to increase the speed in correcting myopia and hypermetropia.

Another object of the invention is to enhance accuracy in correcting myopia and hypermetropia.

These and other objects are attained in the fact that the method of correcting ocular refraction anomalies, according to the invention, consists in making pulsed ultraviolet radiation with a wavelength of 223 nm incident on the surface of the eye, pulse duration being 5 to 50 ns, pulse shape being close to rectangular, simultaneously assigning the distribution of said ultraviolet radiation across the surface of the cornea and evaporating in a lamellar manner the cornea until desired correction of refraction anomalies, in so doing, the density of energy of said ultraviolet radiation is taken in an amount to ensure uniform evaporation of the cornea surface.

It is expedient that up to 10$^4$ pulses of said ultraviolet radiation with a frequency of 5 to 25 Hertz be fed, the density of energy of ultraviolet radiation be taken from 120 to 1200 mJ/cm$^2$, ultraviolet radiation be focused on the surface of the cornea into a spot 3 to 6 mm in diameter, and axisymmetrical distribution of ultraviolet radiation be provided whose exposition would change from the center of the area of the effect of said ultraviolet radiation toward its periphery.

It is also advantageous to feed pulses with a frequency of 10 to 15 Hertz and use the density of energy of ultraviolet radiation from 150 to 600 mJ/cm$^2$ or from 600 to 900 mJ/cm$^2$, focus ultraviolet radiation on the surface of the cornea into a spot 5 mm in diameter.

The foregoing objects are attained also by that a device for correcting ocular refraction anomalies, comprising optically interconnected and successively arranged components such as an ultraviolet pulsed laser, a uniform light beam former, a slotted mask having a slot shaped as a lobe and a drive enabling its rotation, and a means adapted for forming a slotted mask image on the corneal surface and having at its optical outlet a unit used to monitor energy density of ultraviolet radiation supplied to the corneal surface, as well as a microscope used to observe the emission of ultraviolet radiation to the corneal surface and the correction process, said microscope being optically connected with the image former, in which, according to the invention, the slotted mask has at least one more slot shaped as a lobe identical with the first lobe therein, a feature making it possible to obtain, in rotation of the slotted mask, uniform axisymmetric distribution of ultraviolet radiation over the exposed corneal surface, the pulsed laser operating at a wavelength of 223 nm.

It is advantageous that the slotted mask should comprise a substrate having a surface opaque to ultraviolet radiation and slots representing lobes transparent to ultraviolet radiation or a surface transparent to ultraviolet radiation and lobes opaque to ultraviolet radiation, the interface between the opaque surface of the substrate and each transparent lobe or between the transparent surface of the substrate and each opaque lobe being defined as $$\phi = \frac{2\pi}{n}(m-1) \pm \frac{\pi}{n}\left[1 - \left(\frac{r}{r_0}\right)^2\right]$$

where n is the number of lobes of the slotted mask, m is the ordinal number of a respective lobe of the slotted mask, $r_0$ is the length of the lobe, r is radial coordinate of the boundary of each lobe, and $\phi$ is angular coordinate of the boundary of each lobe.

The number of slots in the slotted mask may vary from two to six.

BRIEF DESCRIPTION OF THE DRAWINGS

The invention will now be described further with reference to specific embodiments thereof, taken in conjunction with the accompanying drawings wherein.

DETAILED DESCRIPTION OF THE INVENTION

Figure 1:
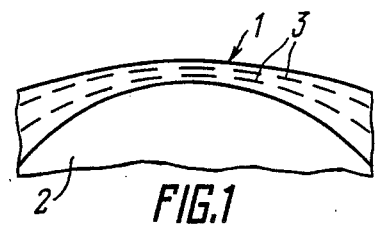
FIG. 1 is a longitudinal section of the cornea changing in the course of correction according to the invention.

A method for correcting eye refraction anomalies consists in making pulsed ultraviolet radiation with a wavelength $\lambda=223$ nm incident on the surface of the cornea. The given wavelength is chosen in view of the results of a series of experiments performed by the inventors when studying the effect of strong ultraviolet radiation on biological tissue. Laser radiation effect on the tissue of the eye anterior chamber (cornea, sclera, conjunctiva) with different wavelength and, what is most important, the study of the process and the results of healing after such effect, show that the speed of evaporation of the biological tissue (the depth of a layer being removed for one pulse) for radiation with a wavelength $\lambda=193$ nm, $\lambda=223$ nm, $\lambda=248$ nm is 0.8 $\mu$m, 2 $\mu$m, and 3 $\mu$m, respectively and in traumaticity, i.e., the thickness of a thermally coagulated layer it corresponds to 1–3 $\mu$m, 1–3 $\mu$m, 10–20 $\mu$m, respectively. Therefore, the radiation with a wavelength of $\lambda=223$ nm, without increasing traumaticity, permits raising the rate of correction.

Radiation pulse length is 5 to 50 ns, a drop in the pulse length involves appreciable difficulties in providing a strong pulse source of ultraviolet radiation with requisite energy of the pulse and negligible duration of the latter. A delay in the pulse over the said limit brings about a higher level of traumaticity of a thermal nature in the layers adjacent to the affected area.

The radiation pulse shape should be close to rectangular. It should be free from overshoots causing uncontrolled removal of the cornea due to a threshold character of evaporation. The presence of "tails" (delaying of pulse edges) leads to the emergence of thermal injuries, i.e., the growth of traumatism.

Radiation is directed to the cornea through a mask, and the radiation is uniformly distributed across the mask surface which is necessary for obtaining a desired profile of the cornea surface.

The radiation energy density on the eye surface is 120 to 1200 mJ/cm$^2$. The loser boundary is associated with the threshold character of evaporation and with energy density values below 120 mJ/cm$^2$ evaporation does not occur for a given wavelength. The upper boundary of energy density of 1200 mJ/cm$^2$ is stipulated by the appearance and rapid growth of traumatism due to overheating of the adjacent layers of the cornea and a stroke effect associated with the character of evaporation.

Depending on the value of refraction anomaly to be corrected, the number of radiation pulses does not exceed $10^4$.

The laser radiation pulse frequency is 5 to 25 Hertz.

Limitation of the negative peaks of frequency is effected to avoid the losses in correction accuracy due to the eye displacement in the process of correction since the human eye is a live object. The limitation of positive peaks of frequency is due to the emergence of a cumulative thermal effect.

The focal spot is 3 to 6 mm in diameter. A smaller diameter of the spot brings about distortion of vision associated with the edge effects in side vision as a result of incomplete correction of the entire visual area of the cornea. A greater diameter fails to substantially improve the correction because it is the excess visual area of the cornea that is corrected, but this leads a quadratic growth of radiation source energy, which fact markedly complicates the construction of a radiation source and makes the whole device more cumbersome and expensive.

It turns out it is expedient that eye refraction anomalies should be corrected with the following parameters of ultraviolet radiation. Energy density is chosen from 150 to 600 mJ/cm$^2$ or from 600 to 900 mJ/cm$^2$, in so doing, the frequency of pulse recurrence is chosen from 10 to 15 Hertz, and the diameter of the spot in which radiation is focused is 5 mm.

On the surface of the cornea the radiation exposition has an axisymmetrical distribution which allows of obtaining a required profile of the cornea surface when correcting refraction anomalies.

The exposition of radiation varies from the center of its effect area toward periphery.

Pulses of almost rectangular shape are incident on the surface 1 (FIGS. 1 or 2) of the cornea 2 and evaporate the latter layer by layer. Provided the change in radiation exposition is such that the exposition grows from the periphery toward the center, in the center of the cornea 2 the thickness of evaporated layer 3 (FIG. 1) is greater than in the periphery and, consequently, evaporation in the center of the cornea 2 is higher. This brings about a general decrease in the curvature of the surface 1 of the cornea 2.

If the exposure to radiation is changed so that it is greater around the periphery of the cornea 2 than in its centre, the thickness of an evaporable layer 3' (FIG. 2) is greater around the periphery whereby the curvature of the surface 1 of the cornea will increase.

So, ocular refraction anomalies may be suitably corrected by changing the radius of curvature of the surface 1 of the cornea 2.

The present invention comprises the emission of ultraviolet radiation to a surface 1 (FIG. 1 or 2) of the cornea 2 and evaporation of the cornea 2 layer by layer. If the exposure to radiation is changed so that it increases from the periphery of the cornea 2 to its centre, the thickness of an evaporable layer 3 (FIG. 1) in the centre of the cornea 2 exceeds its thickness around the periphery and, thus, evaporation of the cornea 2 is greater at its centre. As a result, the curvature of the surface 1 of the cornea 2 will generally be decreased.

The amount of radiation pulses being fed depends on the degree of desired correction and with a chosen wavelength of radiation being 223 nm does not exceed $10^4$, varying from the value of $10^2$ to $10^4$. This is one of the major advantages of the method under consideration because the time of radiation effect on the cornea is reduced with a simultaneous decline in traumatization of biological tissues.

Figure 3:
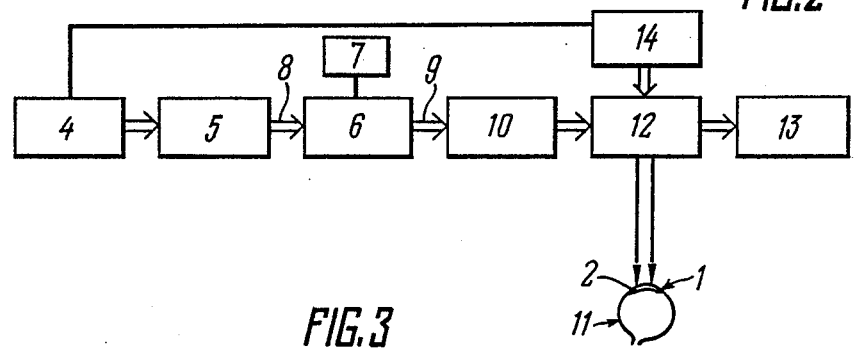
FIG. 3 is a block diagram of a device for correcting ocular refraction anomalies according to the invention.

The device for correcting ocular refraction anomalies in compliance with the invention comprises an ultraviolet pulsed laser 4 (FIG. 3) operating at a wavelength of 223 nm, a uniform light beam former 5 optically connected with the laser 4, a slotted mask 6 provided with a drive 7 enabling its rotation and installed at an optical outlet 8 of the former 5. Disposed at an optical output 9 of the slotted mask 6 is a means 10 adapted for forming the image of the slotted mask 6 on the surface 1 of the cornea 2 of the eye 11. Installed after said forming means along the same optical axis is a microscope 12 used to observe the emission of ultraviolet radiation to the surface 1 of the cornea 2 of the eye 11 and the correction process.

Optically connected with the forming means 10 is a unit 13 designed to monitor energy density of ultraviolet radiation incident on the surface 1 of the cornea 2.

The device comprehended by the invention also includes a unit 14 for controlling the correction process, which is electrically connected to the laser 4.

Figure 4:
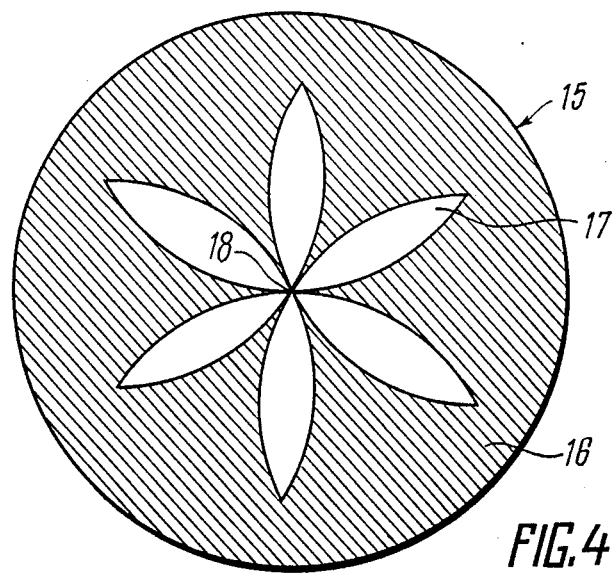
FIG. 4 depicts a slotted mask according to the invention.
Figure 5:
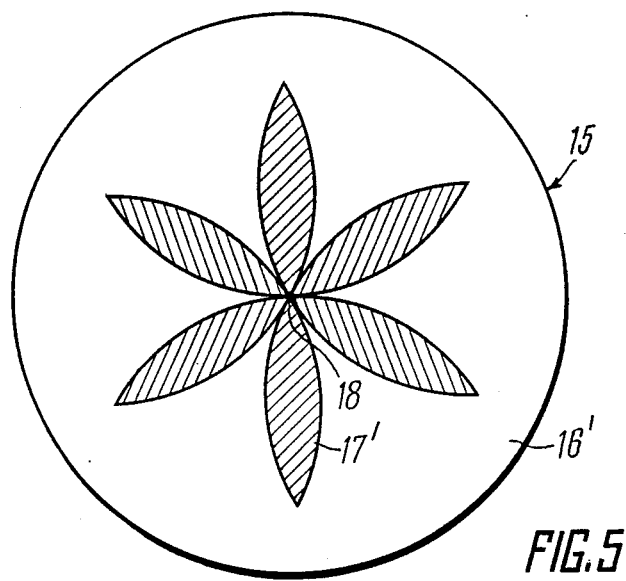
FIG. 5 shows another embodiment of the slotted mask according to the invention.

The slotted mask 6 comprises a substrate 15 (FIG. 4) having a surface 16 opaque to ultraviolet radiation. The substrate 15 has at least two slots representing sections transparent to ultraviolet radiation. These sections are shaped as lobes 17 (FIG. 4). In another embodiment of the invention a surface 16' (FIG. 5) is transparent to ultraviolet radiation and lobes 17' are opaque to said radiation.

The boundary of the lobes 17 (FIGS. 4 and 5), 17' is defined as $$\phi = \frac{2\pi}{n}(m-1) \pm \frac{\pi}{n}\left[1 - \left(\frac{r}{r_0}\right)^2\right] \quad (1)$$

where
n—number of lobes 17 and 17';
m—ordinal number of the respective lobe 17, 17';
$r_0$—length of the lobe 17, 17';
r—distance from a centre 18 of the substrate 15 to any point at the boundary of each lobe 17, 17', that is, radial coordinate of the boundary of any lobe 17, 17';
$\phi$—angular coordinate of the boundary of any lobe 17, 17';

The number of lobes 17 and 17' should desirably be from two to six since the use of one lobe 17, 17' enabling proper correction will make the cornea too thin due to excessive evaporation.

If the number of lobes 17 and 17' exceeds six, there will be difficulties relating to protection of a thin structure of the mask in its central zone and to the effect of a high-power radiation pulse at a high energy density.

Furthermore, at the chosen wavelength of 223 nm excessively large quantity of corneal tissue is evaporated, whereas with the mask comprising more than six lobes the conditions for removing heat from the thin structure of the mask in its central portion are appreciably deteriorated.

Figure 6:
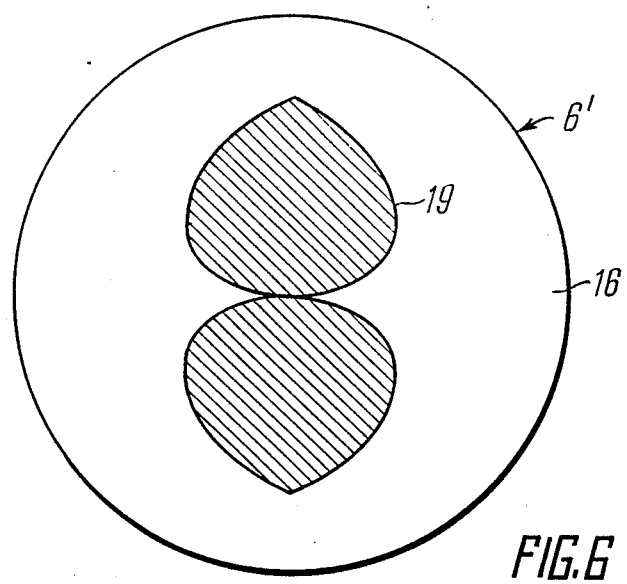
FIG. 6 shows the slotted mask comprising two lobes according to the invention.
Figure 7:
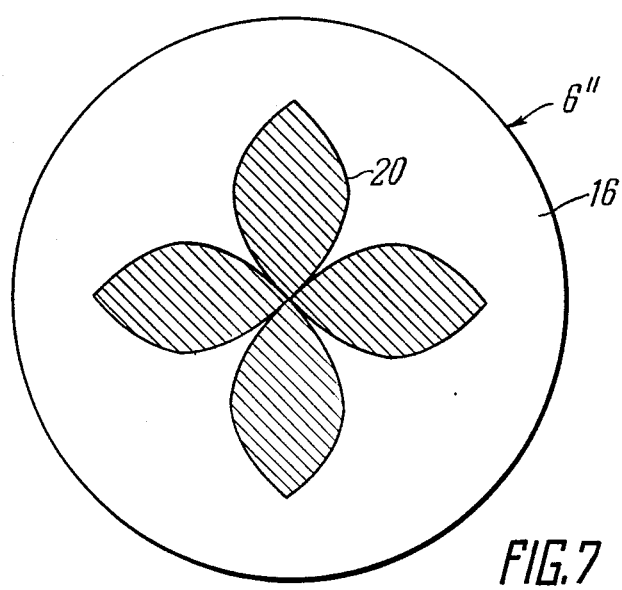
FIG. 7 shows the slotted mask comprising four lobes according to the invention.

FIGS. 6 and 7 show preferred embodiments of the slotted mask 6', 6" which have respectively, two lobes 19 and four lobes 20.

Curves limiting the shape of any of the lobes 17 (FIGS. 4, 5), 17' 19 (FIGS. 6, 7), 20 are determined by reference to the above expression (1).

Figure 8:
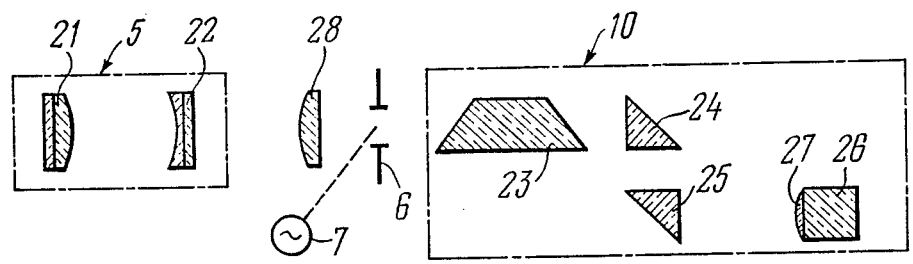
FIG. 8 is a schematic diagram of the device according to the invention.

FIG. 8 shows another embodiment of the device according to the invention.

The former 5 comprises lenses 21 (FIG. 8) and 22. The former 10 comprises prisms 23, 24, 25 and also a prism 26 combined with a lens 27.

A lens 28 is installed in front of the slotted mask 6. The drive 7 of the slotted mask 6 is an electric motor whose shaft is connected with the mask 6.

Figure 9:
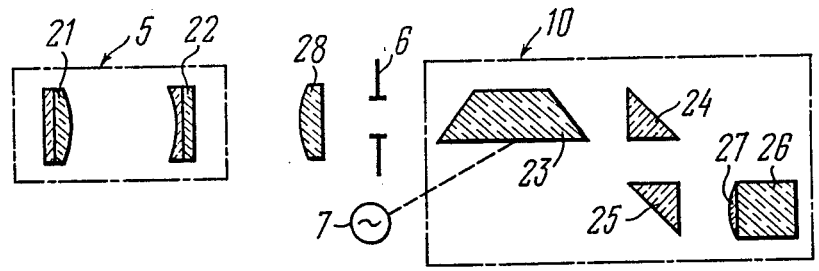
FIG. 9 shows another embodiment of the device according to the invention.

To produce the effect of rotation of the image of the mask 6 (FIG. 9), the drive 7 represents an electric motor having its shaft connected with the prism 23.

The device forming the subject of the present invention operates as follows.

A light beam emitted by the laser 4 at a wavelength of 223 nm is passed through the former 5 with its intensity being sectionally distributed in a uniform manner. A uniform light beam is produced at the outlet of said former. Moreover, the former 5 changes the geometry of the light beam to suit the dimensions of the mask 6. As the mask 6 is rotated by the drive 7, the exposure to radiation supplied via the former 10 to the surface 1 of the cornea 2 changes due to the presence of several slots shaped as lobes in the mask. With the mask 6 comprising transparent lobes 17 (FIG. 4), the exposure decreases from the centre to the periphery, the centre of the affected area being exposed to a larger measure. So, the thickness of the evaporable layer in the centre is greater than around the periphery, a factor generally decreasing the curvature of the surface 1 of the cornea 2.

With the mask 6 comprising opaque lobes 17' (FIG. 5), the exposure increases from the centre of the cornea 2 to its periphery whereby the curvature of the surface 1 of the cornea 2 will increase due to corresponding changes in the thickness of the evaporable layer of the cornea.

Figure 2:
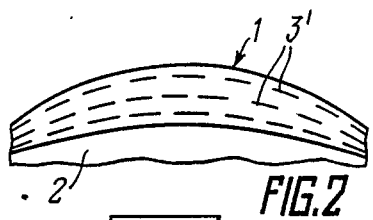
FIG. 2 is a longitudinal section of the cornea changing in the course of correction in another embodiment of the invention.

A light beam passed through the former 10 and the microscope 12 is focused to form a spot 3 to 6 mm in diameter on the surface 1 of the cornea 2. Substantially square pulses fed to the cornea 2 cause its evaporation layer by layer as shown in FIG. 1 or 2, thereby changing the radius of curvature of the corneal surface in the manner described above.

The control unit 14 is used to obtain the required number of pulses varying approximately within $10^2$–$10^4$, a desired energy density from 120 to 1200 mJ/cm$^2$, the pulse recurrence rate from 5 to 25 Hz and the pulse duration from 5 to 50 ns.

The parameters of induced radiation are monitored by the use of the unit 13 which functions in a known manner.

The disclosed method applicable to myopia and hypermetropia is effected in the manner as it outlined in the examples hereinbelow.

EXAMPLE 1

Patient A. suffers from the consequences of apenetrating corneal-scleral injury of the left eye, vast corneal cicatrix accreted with the iris, iris rupture, deformation and displacement of the pupil, film-like semiopacity of the cataract of the left eye. Visual acuity of the left eye: photoperception with a regular light projection. Echobiometry: a plurality of low-amplitude peaks are observed in the vitreous body.

Keratometry: rough irregular astigmatism. The cornea curvature mean radius is 7.5 mm.

The right eye is without pathology. Visual acuity is 1.0.

The patient was operated on for correction of hypermetropia (aphakia) according to the above-identified method.

Laser, excimer; wavelength of 223 nm, pulse length of 5 ns, energy density of 600 mJ/cm$^2$, frequency of 25 Hertz, focal spot 5 mm in diameter. Rotating mask with four opaque lobes.

The laser is focused to the cornea center. Positive meniscus is formed in the centre with a curvature radius of 5.5 mm with moderate irregular astigmatism. Evaporation depth along periphery is 50 μm. Total amount of pulses is $2.7 \times 10^3$.

A therapeutic contact lens with soloxeryl is applied.

EXAMPLE 2

Patient G. Diagnosis: consequences of penetrating injury of the cornea in the right eye, corneal cicatrix, film cataract.

Visual acuity of the right eye: photoperception with regular light projection.

Keratometry: irregular corneal astigmatism, average curvature radius of the cornea center is 8.7 mm. Echobiometry: the eye size is 24.3 mm, vitreous body is normal.

The left eye is without pathology, visual acuity is 1.0.

The patient has been operated on using laser epikeratophakia according to the above-described method.

The laser is excimer, wavelength is 223 nm, pulse length is 25 ns, energy density is 900 mJ/cm$^2$, frequency is 12 Hertz, focal spot is 5 mm in diameter. The rotating mask with six opaque lobes.

The laser is focused to the cornea center. Positive meniscus is formed with a curvature radius of 6.2 mm. Depth of cornea evaporation along periphery is up to 60 μm. Total amount of pulses is $2 \times 10^3$.

A therapeutic contact lens is applied with soloxeryle. Moderate folds of the descement tunic are observed along with surface opacity of the cornea in the zone of laser influence and cornea thinning in periphery, positive meniscus with epithelization in the center.

Complete epithelization of the defect was carried out and a positive meniscus was formed with a curvature radius of 6.4 mm.

The following was extablished as a result of surgical intervention: a positive meniscus with a curvature radius of 6.4 mm in the cornea center; the cornea is transparent in the zone 5 mm in diameter, slight opacity of the stroma under epithelium. Visual acuity of the right eye 0.2, not correctant; the left eye $-1.0$.

The patient is discharged for outpatient treatment.

EXAMPLE 3

Patient K. was admitted with a diagnosis: consequences of penetrating injury of the cornea in the left eye, peripheral vast corneal cicatrix accreted with the iris, deformation of the pupil, traumatic cataract.

Visual acuity of the left eye: photoperception with regular light projection.

Keratometry: irregular astigmatism, average curvature radius of the cornea center is 7.4 mm. Echobiometry: eye size is 23.6 mm, vitreous body is transparent.

Operation was performed using laser epikeratophakia according to the above-described method.

The laser is excimer, wavelength is 223 nm, pulse length is 50 ns, energy density is 1200 mJ/cm$^2$, frequency is 5 Hertz, focal spot is 5 mm in diameter. The rotating mask with two opaque lobes.

The laser is focused to the cornea center, positive meniscus is formed with a curvature radius of 6.0 mm. Depth of evaporation of the cornea tissue along periphery is up to 60 μm. Total amount of pulses is $10^3$.

A soft contact lens with soloxeryle is applied.

The method for correcting myopia is illustrated by the following examples.

The eye operation field is treated in the manner analogous to that during correction of hypermetropia.

EXAMPLE 4

The patient was admitted with a diagnosis: high degree myopia of both eyes, myopic anisometry with a degree of 11.0 diopters.

Refractometry: the right eye $-18.0$ D myopia. The left eye $-7.0$ D myopia.

Keratometry: right eye $-8.42$ mm, left eye $-8.12$ mm.

Echobiometry: right eye $-28.7$ mm, left eye $-25.2$ mm.

Visual acuity: right eye 0.02 with correction $-18.0$ D$=0.2$.

Left eye 0.08 with correction $-7.0$ D$=0.9$.

Correction of OD is intolerable, with tolerable correction $-8.0$ D–0.08.

Operation was performed using laser keratomylesis according to the above-described method. The excimer laser was used, wavelength of 223 nm, pulse length of 50 ns, energy density of 1200 mJ/cm$^2$, frequency of 5 Hertz, focal spot 5 mm in diameter, rotating mask with two lobes.

The operation involved no complications. A defect developed in the central zone of the cornea shaped as a negative meniscus with even edges and deepening of the center to 60 μm. Total number of pulses is $10^3$. A therapeutic contact lens with soloxeryl ointment was applied. Operation is painless.

No pains. The eye is moderately irritated, in the central zone there are observed folds of the descement tunic and a slight opacity of the anterior layers of the stroma in the zone of intervention, epithelization is incomplete.

Afterwards, epithelization is complete, number of folds in the descement tunic decreased. In the light of a slit lamp there is observed a negative meniscus with an opalescent front edge. Opacification of the cornea is not observed visually.

The patient has been discharged for outpatient treatment. Visual acuity of the right eye 0.1, not corrective.

The left eye 0.1 with correction −7.0 D=0.9.

EXAMPLE 5

Patient V. was admitted with a diagnosis: high degree myopia of the left eye, middle-degree myopia of the right eye, myopic anisometry with a degree of 18.5 D.
Refractometry:
  right eye −3.5 D myopia.
  left eye −22.0 D myopia.
Keratometry:
  right eye −7.8 mm.
  left eye −7.4 mm.
Echobiometry:
  right eye −24.2 mm.
  left eye −30.1 mm.

Visual acuity: right eye −0.2 with correction −3.5 D=1, left eye −0.01 with correction −20.0 D=0.1, correction is intolerable, with correction 5.0 D=0.06.

Observed in the fundus of the left eye is an annular myopic staphiloma and atrophic foci in the posterior pole.

The operation using laser keratomylesis of the left eye was performed in keeping with the disclosed method.

The excimer laser was used, wavelength of 223 nm, pulse length of 25 ns, energy density of 900 mJ/cm$^2$, frequency of 12 Hertz, focal spot 5 mm in diameter, rotating mask with six lobes. The laser was focused to the cornea center, a negative meniscus was formed 5 mm in diameter and 60 μm deep in the center. The amount of pulses is $1.2 \times 10^3$. A therapeutic contact lens with soloxeryle ointment is applied.

The patient was discharged for outpatient treatment. The eye is calm. Thinning of stroma is observed through a slit lamp with the formation of a negative meniscus.

Visual acuity: right eye −0.2 with correction −3.5 D=1.0; left eye is not corrected.

Refraction skiascopically −2.0 D myopia with irregular astigmatism.

EXAMPLE 6

Patient S. was admitted with a diagnosis: high degree myopia of the right eye. Myopic anisometry with 15.0 diopters.
Refractometry:
  right eye −15.0 D myopia
  left eye −0.5 D hypermetropia
Keratometry:
  right eye −7.2 mm
  left eye −8.1 mm
Echobiometry:
  right eye −28.3 mm
  left eye −23.4 mm Visual acuity of the right eye is 0.04 with correction −15.0 D=0.4. Left eye 1.0 correction is intolerable. With tolerable correction −4.07 D=0.08.

The operation was performed using laser keratomylesis on the right eye.

Excimer laser was used, wavelength of 223 nm, pulse length of 5 ns, energy density 600 mJ/cm$^2$, frequency of 50 Hertz, focal spot 5 mm in diameter, rotating mask with four lobes. The laser was focused to the cornea center. A negative meniscus was formed with a depth of 40 μm in the center. The amount of pulses is $1.8 \times 10^3$. A therapeutic lens with soloxeryle was applied.

When the patient was discharged his right eye was calm, slight opalescence of the front layers of stroma under epithelium was observed.

Visual acuity of the right eye −0.3, not corrective. Thinning of the cornea by 30 μm.

EXAMPLE 7

Patient K. was admitted with a diagnosis: consequences of penetrating injury of the cornea, corneal cicatrix, deformation of the pupil, traumatic film-like cataract of the left eye.

Visual acuity of the right eye is 1.0. Refraction $\epsilon_m$. The fundus of the eye is without pathology.

The left eye: visual acuity and photoperception with regular light projection. Echobiometry: the eye size is 23.8 mm, single low-amplitude echopics are observed in the vitreous body.

Keratometry: irregular rough astigmatism.

Biomicroscopy: corneal cicatrix 6 mm long, paracentral, deformation of the pupil, film-like cataract.

Operation using laser epikeratophakia was performed according to the disclosed method.

Parameters: excimer laser, wavelength of 223 nm., pulse length of 5 ns, energy density of 1000 mJ/cm$^2$, frequency of 15 Hertz, focal spot 6 mm in diameter, rotating mask with six lobes.

A positive meniscus was formed with a 6 mm diameter in the central zone, curvature radius of 6.5 mm. In the central zone the cornea is clear. Cloud-like surface opacification is observed along periphery.

Operation was performed to extract the traumatic cataract with front vitreoectomy without complications.

The eye is calm. Visual acuity is 0.3 not corrective. Curvature radius of the central zone is 6.5 mm.

EXAMPLE 8

Patient P. was admitted with a diagnosis: penetrating corneal-scleral injury of the right eye, corneal cicatrix, aphakia, destruction of the vitreous body, deformation of the pupil. No pathology is observed in the left eye, visual acuity is 1.0. The fundus of the eye is normal. The right eye: a corneal-scleral cicatrix 5 mm long with the transition to the central zone. Keratometry: rough irregular astigmatism.

Operation was performed using laser epikeratophakia according to the disclosed method.

Excimer laser, wavelength of 223 nm, energy density of 750 mJ/cm$^2$, pulse frequency recurrence 10 Hertz, focal spot 6 mm in diameter, amount of pulses is $1.6 \times 10^3$.

A positive meniscus is formed 6 mm in diameter with a curvature radius of 6 mm.

Healing of the defect after 7 days with complete epithelization and transparent central zone and annular opacification in periphery. A decline in astigmatism in the central zone.

Examination after 1 month. The eye is calm, curvature radius in the cornea center is 6.2 mm, astigmatism in 3.0 incorrect.

Visual acuity of the right eye is 0.2, not corrective.

EXAMPLE 9

Patient B. was admitted with a diagnosis: high-degree hypermetropia of the left eye, hypermetropic astigmatism with oblique axes, anisometropia.

The right eye: visual acuity 1.0, refraction $\epsilon m$. Echobiometry: 23.9 mm. Media are clear.

The left eye: visual acuity 0.08 not corrective. Echobiometry: 22.4 mm, refractometry: 30°−Hm 5.0, 120°−HM 8.0.

Operation with laser epikeratophakia was performed.

Excimer laser, wavelength of 223 nm. Parameters: energy density of 120 mJ/cm$^2$, recurrence frequency of 20 Hertz, the mask with six opaque lobes, focal spot 6 mm in diameter, amount of pulses is $3.4 \times 10^3$.

Healing in the course of seven days.

The eye is calm. The cornea central zone curvature radius is 7.2 mm, slight astigmatism, Refraction: 35°−Hm 1.0; 125°−Hm 1.5.

Visual acuity of the right eye is 1.0, left eye is 0.3, not corrective.

EXAMPLE 10

Patient B. was admitted with a diagnosis: high degree myopia of the right eye, anisometropia, myopic astigmatism. The left eye: visual acuity 0.2 with correction −4.0 D=1.0. Refraction −4.5 mm. Echobiometry: 25.2 mm. Keratometry is 42.0 D. The right eye: visual acuity 0.04 with correction −12.0 D=0.5. Keratometry: 0°=43.5 D, 90°=46.2 D. Refractometry: 0°=12.0 90°=15; echobiometry: 27.5 mm.

Operation using laser keratomylesis was performed on the right eye.

Excimer laser, wavelength is 223 nm, energy density is 300 mJ/cm$^2$, pulse length is 5 ns, focal spot 5 mm in diameter, mask with four lobes, the number of pulses is $2.8 \times 10^3$, frequency of 20 Hertz.

A negative meniscus was formed with depth in the center of 25 µm and 5 mm in diameter.

Healing in the course of seven days.

Epithelization is complete, pronounced opacification of stroma front layers is observed in the central zone. Visual acuity of the right eye 0.2, not corrective. Visual acuity 0.2 with correction −3.5 D=0.5.

EXAMPLE 11

Patient Yu. was admitted with a diagnosis: high degree myopia of the right eye, anisometropia.

No pathology is observed in the left eye, visual acuity is 1.0; refraction: emmetropia.

The right eye: 13.0° myopia. Keratometry is 46.0 D. Echobiometry: 27 mm. Myopic changes are observed in the fundus of the eye. Visual acuity 0.04 with correction −12.0 D=0.7, correction is intolerable.

Operation using laser keratomylesis was performed on the right eye. Excimer laser, wavelength of 223 nm, pulse length is 5 ns, energy density is 800 mJ/cm$^2$, focal spot 5 mm in diameter, $8 \times 10^2$ pulses, frequency of 25 Hertz.

The operation involved no complications. A negative meniscus was formed 50 µm deep in the center.

Healing after 10 days, epithelization complete, cloudlike opacity in the center.

Visual acuity of the right eye 0.3 is not corrective. Slight opacity in the center of the cornea, visual acuity of the left eye is 0.5 not corrective.

EXAMPLE 12

Patient A. was admitted with a diagnosis: high degree myopia of the left eye, anisometropia.

The right eye: visual acuity 1.0, refraction $\epsilon_m$, echobiometry: 24.2 mm, media area clear.

The left eye: visual acuity 0.02 with correction −22.0 D=0.2, correction is intolerable. Myopic changes are observed in the fundus of the eye.

Operation with laser keratomylesis was performed on the left eye according to the disclosed method.

Excimer laser, wavelength of 223 nm, pulse length is 5 ns, energy density of 450 mJ/cm$^2$, number of pulses is $2.6 \times 10^3$, frequency of 5 Hertz, mask with six lobes.

The operation caused no complications. A negative meniscus 50 µm deept is formed in the central zone.

Visual acuity of the right eye 1.0, left eye 0.1 not corrective.

The present invention has been used in operations involving eight patients having high degree of myopia and hypermetropia of the eye, in which conventional methods of correction are ineffective. As a result of the correction of said anomalies the patients' eyesight has been appreciably improved.

The present invention allows correction of ocular refraction anomalies in the case of hypermetropia and myopia without causing any deviation of the ablation region from an ideal circle and prevents the occurrence of astigmatism and other undesirable phenomena.

Moreover, the proposed device makes it possible to restore ocular functions in the event of high myopia and hypermetropia. The indications for its use are the following refraction anomalies: high myopia and hypermetropia, aphacia, astigmatism. The counterindications are progressive myopia and degeneration of the cornea.

We claim:

1. A method for correcting ocular refraction anomalies, which comprises making pulsed ultraviolet radiation with a 223 nm wavelength and a 5 to 50 ns pulse length incident on the surface of the eye, said pulse having the shape close to rectangular, simultaneously assigning the distribution of said ultraviolet radiation across the surface of the cornea and evaporating the cornea in lamellae until a desired correction of refraction anomalies is obtained, in so doing, the density of energy of said ultraviolet radiation is taken such as to ensure uniform evaporation of the surface of the cornea.

2. A method as claimed in claim 1, which comprises feeding of up to 10$^4$ pulses of said ultraviolet radiation.

3. A method as claimed in claim 1, which comprises feeding the pulses of said ultraviolet radiation with a frequency of 5 to 25 Hz.

4. A method as claimed in claim 1, which comprises taking the density of energy of said ultraviolet radiation in an amount from 120 to 1200 mJ/cm$^2$.

5. A method as claimed in claim 1, which comprises focusing said ultraviolet radiation on the surface of the cornea into a spot 3 to 6 mm in diameter.

6. A method as claimed in claim 1, which comprises ensuring axisymmetrical distribution of said ultraviolet radiation whose exposition varies from the center of the area of the effect of said ultraviolet radiation toward its periphery.

7. A method as claimed in claim 2 or 3 or 5 or 6, which comprises taking the density of energy of said ultraviolet radiation from 120 to 1200 mJ/cm$^2$.

8. A method as claimed in claim 2 or 4, or 5, or 6, which comprises feeding the pulses of said ultraviolet radiation with a frequency of 5 to 25 Hertz.

9. A method as claimed in claim 2 or 3, or 4, or 6, which comprises focusing said ultraviolet radiation on the surface of the cornea into a spot 3 to 6 mm in diameter.

10. A method as claimed in claim 2 or 3, or 4, or 5, which comprises ensuring axisymmetrical distribution of said ultraviolet radiation whose exposition varies from the center of the area of the effect of said ultraviolet radiation toward its periphery.

11. A method as claimed in claim 3 or 4, or 5, or 6, which comprises feeding the pulses of said ultraviolet radiation with a frequency of 10 to 15 Hertz.

12. A method as claimed in claim 4, or 5, or 6, which comprises taking the density of energy of said ultraviolet radiation from 150 to 600 mJ/cm$^2$.

13. A method as claimed in claim 4 or 5, or 6, which comprises taking the density of energy of said ultraviolet radiation from 600 to 900 mJ/cm$^2$.

14. A method as claimed in claim 5 or 6, which comprises focusing said ultraviolet radiation on the surface of the cornea into a spot 5 mm in diameter.

15. A method as claimed in claim 7, which comprises taking the density of energy of said ultraviolet radiation from 150 to 600 mJ/cm$^2$.

16. A method as claimed in claim 7, which comprises taking the density of energy of said ultraviolet radiation from 600 to 900 mJ/cm$^2$.

17. A method as claimed in claim 8, which comprises feeding the pulses of said ultraviolet radiation with a frequency of 10 to 15 Hertz.

18. A method as claimed in claim 9, which comprises focusing said ultraviolet radiation on the surface of the cornea into a spot 5 mm in diameter.

19. A method for correcting ocular refraction anomalies, which comprises feeding to the eye surface of pulsed ultraviolet radiation, 223 nm wavelength, 600 to 1200 mJ/cm$^2$ energy density, 5 to 50 ns pulse length with frequency recurrence of 5 to 25 Hertz and the pulse shape close to rectangular, simultaneously ensuring axisymmetrical distribution on the cornea surface of said ultraviolet radiation whose exposition varies from the center of the area of the effect of said ultraviolet radiation toward its periphery, focusing said ultraviolet radiation on the surface of the cornea into a spot and evaporating in lamellae the cornea until a desired correction of ocular refraction anomalies is obtained.

20. A method as claimed in claim 19, which comprises feeding up to 10$^4$ pulses of said ultraviolet radiation.

21. A method as claimed in claim 19 or 20, which comprises taking the density of energy of said ultraviolet radiation from 600 to 900 mJ/cm$^2$.

22. A method as claimed in claim 19 or 20, which comprises feeding pulses of said ultraviolet radiation with a frequency of 10 to 15 Hertz.

23. A method as claimed in claim 19 or 20, which comprises focusing said ultraviolet radiation into a spot 5 mm in diameter.

24. A method as claimed in claim 21, which comprises feeding pulses of said ultraviolet radiation with a frequency of 10 to 15 Hertz.

25. A method as claimed in claim 24, which comprises focusing said ultraviolet radiation into a spot 5 mm in diameter.

26. A device for correcting ocular refraction anomalies, comprising:
an ultraviolet pulsed laser operating at a wavelength of 223 nm;
a uniform light beam former optically connected with said pulsed laser;
a slotted mask optically connected with said uniform light beam former from which a uniform light beam is projected on said slotted mask and having at least two slots, each of which is shaped as a lobe;
a drive for rotating said slotted mask providing for uniform axisymmetric distribution of ultraviolet radiation over the exposed surface of the cornea;
a means for forming an image of said slotted mask on the corneal surface, said means for forming the image on the corneal surface, positioned at the same optical axis with said slotted mask and having an optical outlet;
a unit to monitor energy density of ultraviolet radiation incident on the corneal surface arranged at said optical outlet of said means for forming the image; a microscope to observe the emission of ultraviolet radiation to the surface of the cornea and the correction process, said microscope being optically connected with said slotted mask image former.

27. A device as claimed in claim 26, wherein the slotted mask comprises a substrate having a surface opaque to ultraviolet radiation, while all the slots are shaped as lobes transparent to ultraviolet radiation, the interface between the opaque surface of the substrate and each transparent lobe being defined as $$\phi = \frac{2\pi}{n}(m-1) \pm \frac{\pi}{n}\left[1 - \left(\frac{r}{r_0}\right)^2\right],$$

where n is the number of lobes in the slotted mask, m is the ordinal number of a respective lobe of the slotted mask, $r_0$ is the length of the lobe, r is radial coordinate of the boundary of each lobe, $\phi$ is angular coordinate of the boundary of each lobe, $1 \leq m \leq n$.

28. A device as claimed in claim 26, wherein the slotted mask comprises a substrate having a surface transparent to ultraviolet radiation, while all the lobes are opaque to ultraviolet radiation, the interface between the transparent surface of the substrate and each opaque lobe being defined as $$\phi = \frac{2\pi}{n}(m-1) \pm \frac{\pi}{n}\left[1 - \left(\frac{r}{r_0}\right)^2\right],$$

wherein n is the number of lobes of the slotted mask, m is the ordinal number of a respective lobe of the slotted mask, $r_0$ is the length of the lobe, r is radial coordinate of the boundary of each lobe, $\phi$ is angular coordinate of the boundary of each lobe, $1 \leq m \leq n$.

29. A device as claimed in any of the preceding claims from 26 to 28, wherein the number of slots in the slotted mask varies from two to six.

* * * * *